(12) United States Patent
Alansari et al.

(10) Patent No.: US 11,304,845 B1
(45) Date of Patent: *Apr. 19, 2022

(54) METHOD OF TREATING OBSTRUCTIVE SLEEP APNEA AND SNORING AND A DENTAL APPLIANCE THEREFORE

(71) Applicant: King Abdulaziz University, Jeddah (SA)

(72) Inventors: Reem Ahmed Othman Alansari, Jeddah (SA); Rodrigo Ernesto Gamarra Salazar, Jeddah (SA); J. Felipe Aguirre, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/139,285

(22) Filed: Dec. 31, 2020

(51) Int. Cl.
*A61F 5/56* (2006.01)

(52) U.S. Cl.
CPC .................................. *A61F 5/566* (2013.01)

(58) Field of Classification Search
CPC ...... A61F 5/56; A61F 5/566; A61F 2005/563; A61C 7/08; A61C 7/36; A63B 71/085; A63B 2071/086; A63B 2071/088; A61M 16/0488; A61M 16/049
USPC ........ 128/848, 859, 861, 862; 433/6, 19, 24, 433/140
See application file for complete search history.

(56) References Cited

U.S. PATENT DOCUMENTS

| | | | |
|---|---|---|---|
| 8,156,940 B2* | 4/2012 | Lee ........................ | A61F 5/566 128/848 |
| 8,631,800 B2* | 1/2014 | Lindsay .................. | A61F 5/566 128/848 |
| 2008/0199824 A1 | 8/2008 | Hargadon | |
| 2008/0202530 A1 | 8/2008 | Sims et al. | |
| 2010/0065067 A1 | 3/2010 | Lee | |
| 2011/0017220 A1* | 1/2011 | Lindsay .................. | A61F 5/566 128/848 |
| 2011/0030704 A1* | 2/2011 | Hanna ...................... | A61C 7/08 128/861 |
| 2014/0120489 A1* | 5/2014 | Klein ....................... | A61C 7/08 433/6 |
| 2014/0352700 A1* | 12/2014 | Ingemarsson-Matzen .................. | A61F 5/566 128/848 |

(Continued)

FOREIGN PATENT DOCUMENTS

EP 3 427 704 A1 1/2019

*Primary Examiner* — Alireza Nia
*Assistant Examiner* — Robin Han
(74) *Attorney, Agent, or Firm* — Oblon, McClelland, Maier & Neustadt, L.L.P.

(57) ABSTRACT

An adjustable dental appliance having an upper tray and a lower tray is provided. The upper tray includes an upper dentition-interfacing layer and an upper support layer. The upper support layer has indentation tracks oriented in a mediolateral direction when an arch shape of the upper tray is aligned with an upper dental arch. The lower tray includes a lower dentition-interfacing layer and a lower support layer. The lower support layer has rails attached to an upper surface thereof and oriented in a mediolateral direction when an arch shape of the lower tray is aligned with a lower dental arch. The rails of the lower tray fit securely into the indentation tracks of the upper tray and thereby interlock the upper tray and lower tray.

11 Claims, 6 Drawing Sheets

(56) References Cited

U.S. PATENT DOCUMENTS

2016/0095740 A1* 4/2016 Mardirossian .......... A61F 5/566
                                                    128/847
2017/0035533 A1   2/2017 Ross
2019/0021901 A1   1/2019 Leblanc et al.

* cited by examiner

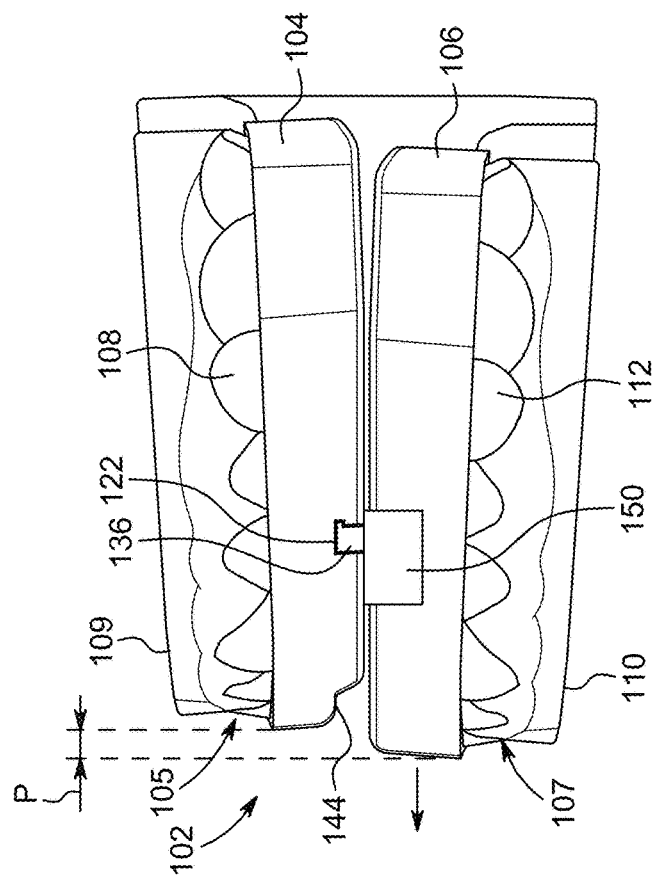
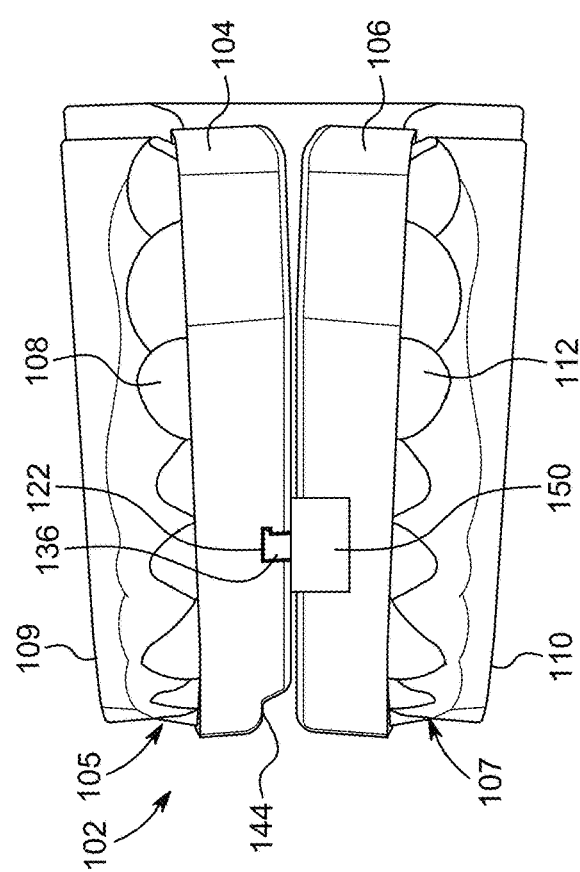

METHOD OF TREATING OBSTRUCTIVE SLEEP APNEA AND SNORING AND A DENTAL APPLIANCE THEREFORE

BACKGROUND OF THE INVENTION

Field of the Invention

The present disclosure relates to dental appliances and, more particularly relates, to an adjustable dental appliance and method of treating obstructive sleep apnea and snoring using adjustable dental appliance.

Discussion of the Background

Sleep apnea is a potentially serious sleep disorder in which a person's breathing repeatedly stops and starts while sleeping. While there are a number of types of sleep apnea, the most common is obstructive sleep apnea. Obstructive sleep apnea arises when the muscles of the jaw and throat relax while sleeping, allowing the airway to be partially or completely obstructed by the soft tissues of the mouth and throat such as the tongue and soft palate. Obstructive sleep apnea is particularly common in individuals who sleep on their back in a supine position. When a person is in such a position, relaxation of the jaw and throat muscles causes the jaw to sag or fall in a dorsal direction. This natural sagging causes the tongue and other soft tissues to fall to the back of the throat, leading to obstruction of the airway. The muscle relaxation also allows the soft tissues of the mouth and throat to vibrate when air passes over them as part of breathing. This vibration causes a hoarse or harsh sound known as snoring. Due to the similar causes, snoring and obstructive sleep apnea are very commonly associated with one another.

One method used to treat both snoring and obstructive sleep apnea is to prevent the sagging of the relaxed jaw. Such prevention involves holding the jaw forward in a ventral direction. This physical holding of the jaw in a ventral direction is frequently referred to as advancement of the mandible. A mandible held in an advanced (or ventral) position does not allow the tongue or soft tissues to sag far enough to obstruct the airway. This mandibular advancement is typically achieved by the use of dental appliances placed in the mouth when a patient goes to sleep. Such dental appliances may include an upper component to accommodate the upper (maxillary) teeth and a lower component to accommodate the lower (mandibular) teeth. Typically, such dental appliances work to position the mandible forward from a neutral mandible position. Additionally, in such dental appliances, the upper component and lower component are typically fused each other. The fused arrangement prevents the mandible from moving side-to-side (mediolateral direction). The position forward from neutral and the restriction of lateral motion can be very uncomfortable to patients. Sometimes, this unnatural positioning and restriction also creates problems for patients such as irritation or jaw pain. In addition to patient comfort, freedom of lateral mandibular movement is necessary for patients who suffer from sleep bruxism, and claustrophobic patients may experience anxiety if the mandible is fixed in one position. Sleep bruxism is defined as a movement disorder characterized by rhythmic masticatory muscle activity associated with tooth grinding. Such discomfort, disadvantageous in and of itself, can lead to inefficient use that decreases effectiveness or may cause the patient to stop using the device altogether, even against the advice of a medical professional.

Many currently available devices are non-adjustable. Patents must choose from a range of sizes based on the whims of a manufacturer, not the needs of their anatomy. Alternatively, a device may be custom fitted to a patent, a costly and labor intensive process. If the needs of the patient change, however, an entirely new device would have to be custom fitted. An efficient and reliable dental appliance that maintains a proper forward position of the mandible, allows the jaw to move in a mediolateral direction, and is easily adjustable to meet the needs of a patient's anatomy would represent a significant improvement over available devices for treating obstructive sleep apnea and snoring.

SUMMARY OF THE INVENTION

In one aspect, the present disclosure relates to an adjustable dental appliance. The adjustable dental appliance comprises an upper tray having an upper dentition-interfacing layer and an upper support layer and a lower tray having a lower dentition-interfacing layer and a lower support layer. The upper tray has an arch shape, and the upper support layer includes one or more indentation tracks oriented in a substantially mediolateral direction when the arch shape of the upper tray is aligned with an upper dental arch. The lower tray has an arch shape, and the lower support layer includes one or more rails attached to an upper surface of the lower support layer oriented in a substantially mediolateral direction when the arch shape of the lower tray is aligned with a lower dental arch. The one or more rails of the lower tray fit securely into the one or more indentation tracks of the upper tray, thereby interlocking the upper tray and lower tray In some embodiments, the one or more rails of the lower tray fit securely into the one or more indentation tracks of the upper tray such that the one or more rails can move along a length of the indentation track.

In some embodiments, the one or more rails of the lower tray fit securely into the one or more indentation tracks of the upper tray such that a jaw fitted with the adjustable dental appliance is permitted to move in a side-to-side motion.

In some embodiments, the one or more rails of the lower tray fit securely into the one or more indentation tracks of the upper tray such that the jaw fitted with the adjustable dental appliance is inhibited from depression/elevation jaw motions and/or protrusion/retraction jaw motions.

In some embodiments, indentation track or tracks are unobstructed thereby permitting the one or more rails to pass through the entirety of the length of the one or more indentation tracks and enter or exit the one or more indentation tracks via a left track end and a right track end.

In some embodiments, the lower tray comprises an array of attachment points to which the one or more rails are affixed. The array of attachment points allows for adjustment of the positioning of the one or more rails on the lower support layer.

In some embodiments, adjustment of the positioning of the one or more rails on the lower support layer changes a protrusive orientation of the lower dental arch to the upper dental arch of a patient fitted with the adjustable dental appliance.

In some embodiments, the array has an attachment point spacing of 0.5 to 2.0 mm.

In some embodiments, the array allows for adjustment of the protrusive orientation of the lower dental arch to the upper dental arch of the patient fitted with the adjustable dental appliance by 2.5 to 15 mm.

In some embodiments, the upper dentition-interfacing layer conforms to an upper dentition.

In some embodiments, the lower dentition-interfacing layer conforms to a lower dentition.

In some embodiments, the upper support layer and/or the lower support layer comprises a metal sub-layer.

In one embodiment, the upper dentition-interfacing layer and/or the lower dentition-interfacing layer comprises a biocompatible polymer.

In some embodiments, the biocompatible polymer is at least one selected from the group consisting of a nylon, a polyolefin, a polyolefin-vinyl acetate copolymer, and a polyacrylate.

The present disclosure also relates to a method of treating obstructive sleep apnea. The method comprises fitting a patient with the adjustable dental appliance, which is in an interlocked configuration, such that the upper dentition-interfacing layer interfaces with the patient's upper dentition and the lower dentition-interfacing layer interfaces with the patient's lower dentition.

In some embodiments, the adjustable dental appliance positions the patient's jaw so as to alleviate airway obstruction.

In some embodiments, the method further comprises adjusting a positioning of the one or more rails on the lower support layer to adjust a position of the patient's jaw. The present disclosure also relates to a method of treating snoring. The method comprises fitting a patient with the adjustable dental appliance, which is in an interlocked configuration, such that the upper dentition-interfacing layer interfaces with the patient's upper dentition and the lower dentition-interfacing layer interfaces with the patient's lower dentition.

In some embodiments, the adjustable dental appliance positions the patient's jaw so as to alleviate airway obstruction.

In some embodiments, the method further comprises adjusting a positioning of the one or more rails on the lower support layer to adjust a position of the patient's jaw.

These and other aspects and features of non-limiting embodiments of the present disclosure will become apparent to those skilled in the art upon review of the following description of specific non-limiting embodiments of the disclosure in conjunction with the accompanying drawings.

BRIEF DESCRIPTION OF THE DRAWINGS

A better understanding of embodiments of the present disclosure (including alternatives and/or variations thereof) may be obtained with reference to the detailed description of the embodiments along with the following drawings, in which:

FIG. 5A illustrates an interlocked configuration of the adjustable dental appliance at a neutral position thereof, according to an embodiment of the present disclosure;

FIG. 5B illustrates an interlocked configuration of the adjustable dental appliance at an adjusted position thereof, according to an embodiment of the present disclosure.

DETAILED DESCRIPTION

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

Figure 1:
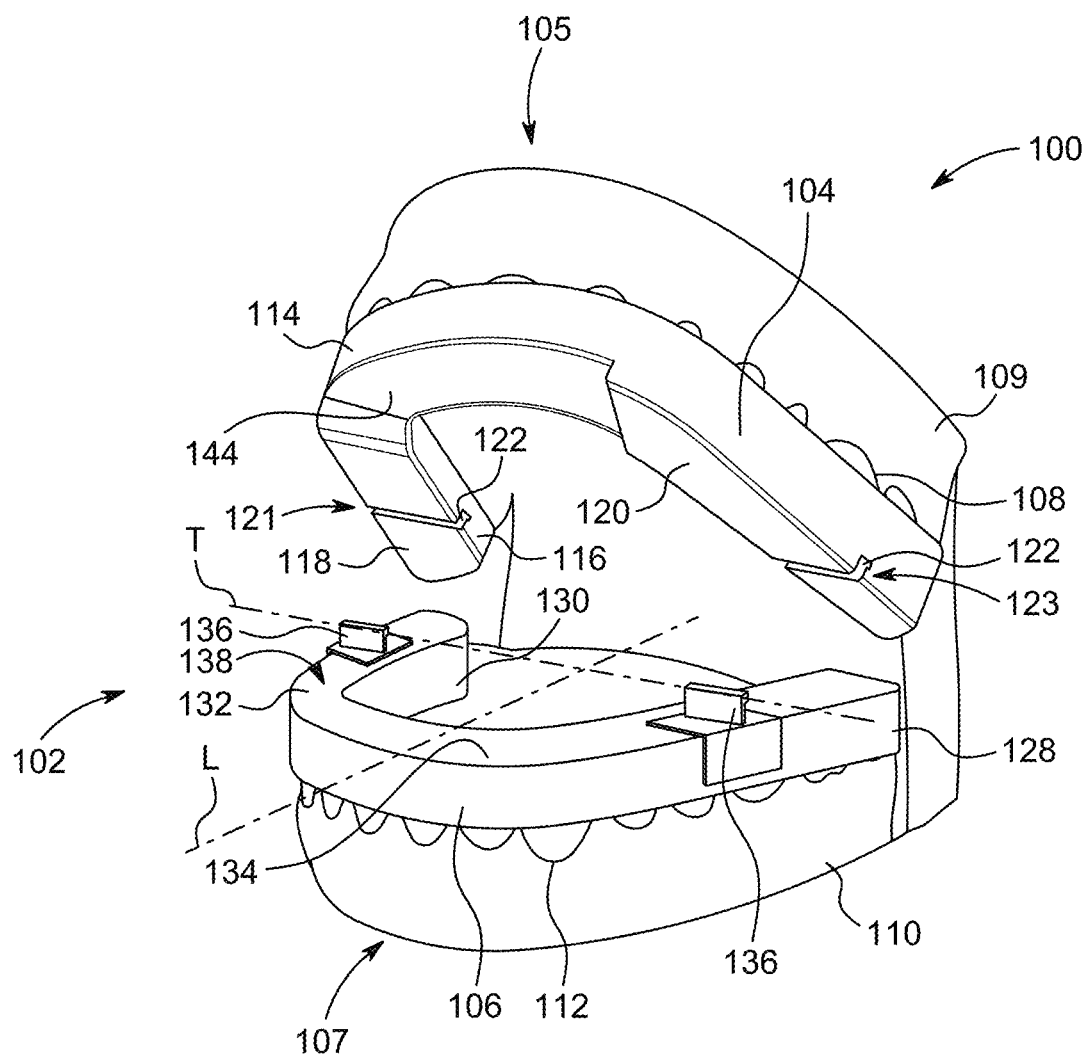
FIG. 1 illustrates a perspective view of an exemplary jaw fitted with an adjustable dental appliance having an upper tray and a lower tray, according to an embodiment of the present disclosure.

FIG. 1 illustrates a perspective view of an exemplary jaw 100 of a patient fitted with an adjustable dental appliance 102, according to an embodiment of the present disclosure. The adjustable dental appliance 102 includes an upper tray 104 and a lower tray 106. Each of the upper tray 104 and the lower tray 106 has an arch shape to align with an upper dental arch 105 and a lower dental arch 107, respectively. Particularly, the upper tray 104 is fitted with an upper jaw 109 and configured to engage with an upper dentition 108 and the lower tray 106 is fitted with a lower jaw 110 and configured to engage with a lower dentition 112. The upper dentition 108 may refer to a structure and a shape of maxillary teeth and the lower dentition 112 may refer to a structure and a shape of mandibular teeth. The adjustable dental appliance is shown in FIG. 1 in a non-interlocked (separated) configuration.

In some embodiments, the upper tray 104 may include an outer side wall 114, an inner side wall 116 and a bottom wall 118 extending between the outer side wall 114 and the inner side wall 116. In some embodiments, the outer side wall 114, the inner side wall 116 and the bottom wall 118 may be together configured to define a U shape cross section for the upper tray 104 to attach with the upper dentition 108. In some embodiments, the upper tray 104 may include the bottom wall 118 and one of the outer side wall 114 and the inner side wall 116. The upper tray 104 comprises an upper dentition-interfacing layer 115 (shown in FIG. 2) and an upper support layer 120. The upper dentition-interfacing layer 115 may refer to an inner surface of the upper tray 104 and conforms to the structure and the shape of the upper dentition 108. Particularly, the upper dentition-interfacing layer 115 may be defined to at least partly enclose and abut an occlusal surface of the maxillary teeth. In some embodiments, the upper dentition-interfacing layer 115 may also at least partly enclose and abut one or both of an outer (or buccal) surface and an inner (or lingual) surface of the maxillary teeth. The upper support layer 120 may refer to an outer surface of the upper tray 104. In some embodiments, the outer side wall 114, the inner side wall 116, or both is part of the upper support layer. In alternative embodiments, the outer side wall 114, the inner side wall 116, or both is part of the upper dentition-interfacing layer. In some embodiments, the upper support layer 120 may include a metal sub-layer (not shown). The metal sub-layer may be used to provide rigidity or other structural integrity to the construction and shape of the upper tray 104. The metal sub-layer may be embedded within the upper tray 104. In some embodiments, the metal sub-layer may be provided in the bottom wall 118 of the upper tray 104. In some embodiments, the metal sub-layer may be provided in one or both of the outer side wall 114 and the inner side wall 116 of the upper tray 104. In some embodiments, the upper dentition-interfacing layer 115 and the upper support layer 120 may be together configured to define the U shape cross section for the upper tray 104 to attach with the upper dentition 108.

The upper support layer 120 of the upper tray 104 includes one or more indentation tracks 122. The indentation track 122 may be defined as a void or a groove in the upper support layer 120. The upper tray 104 may be defined as two equal or symmetrical halves with respect to a longitudinal axis 1' of the jaw 100. In some embodiments, each half of the upper tray 104 includes at least one indentation track 122. In some embodiments, a symmetrical orientation of the indentation tracks 122 is defined on the upper tray 104 with respect to the longitudinal axis Particularly, one indentation track 122 is positioned at right side of the upper tray 104 symmetrically with respect to the indentation track 124 positioned at left side of the upper tray 104. The indentation track 122 provided at the right side of the upper tray 104 may define a right track end 121. The indentation track 122 provided at the left side of the upper tray 104 may define a left track end 123. In some embodiments, the indentation track 122 at the right track end 121 and the left track end 123 of the upper tray 104 may be aligned each other along a transverse axis 'T' of the jaw 100, in which the transverse axis 'T' is perpendicular to the longitudinal axis 'L'. In some embodiments, there may be more than one indentation track 122 at each of the right side and the left side of the upper tray 104.

The adjustable dental appliance 102 further includes the lower tray 106. In some embodiments, the lower tray 106 may include an outer side wall 128, an inner side wall 130 and a top wall 132 extending between the outer side wall 128 and the inner side wall 130. In some embodiments, the outer side wall 128, the inner side wall 130 and the top wall 132 are together configured to define a U shape cross section for the lower tray 106 to attach with the lower dentition 112. In some embodiments, the lower tray 106 may include the top wall 132 and one of the outer side wall 128 and the inner side wall 130. The lower tray 106 further includes a lower dentition-interfacing layer 131 (shown in FIG. 3) and a lower support layer 134. The lower dentition-interfacing layer 131 may refer to an inner surface of the lower tray 106 and conforms to the structure and the shape of the lower dentition 112. Particularly, the lower dentition-interfacing layer 131 may be defined to at least partly enclose and abut an occlusal surface of the mandibular teeth. In some embodiments, the lower dentition-interfacing layer 131 may also at least partly enclose and abut one or both of an outer (or buccal) surface and an inner (or lingual) surface of the mandibular teeth. The lower support layer 134 may refer to an outer surface of the lower tray 106. In some embodiments, the outer side wall 128, the inner side wall 130, or both is part of the lower support layer. In alternative embodiments, the outer side wall 128, the inner side wall 130, or both is part of the lower dentition-interfacing layer. In some embodiments, the lower support layer 134 includes the metal sub-layer. The metal sub-layer may be used to provide rigidity or other structural integrity to the construction and shape of the lower tray 106. The metal sub-layer may be embedded within the lower tray 106. In some embodiments, the metal sub-layer may be provided in the top wall 132 of the lower tray 106. In some embodiments, the metal sub-layer may be provided in the outer side wall 128 and the inner side wall 130 of the lower tray 106. In some embodiments, the lower dentition-interfacing layer 131 and the lower support layer 134 may be together configured to define the U shape cross section for the lower tray 106 to attach with the lower dentition 112.

The lower support layer 134 of the lower tray 106 includes one or more rails 136 attached to an upper surface 138 of the lower support layer 134. The longitudinal axis 1' of the jaw 100 may define the lower tray 106 as two equal or symmetrical halves. In some embodiments, each half of the lower tray 106 may include at least one rail 136. In some embodiments, a symmetric orientation of the rails 136 may be defined on the lower tray 106 with respect to the longitudinal axis 'L'. In some embodiments, at least one rail 136 may be positioned at right side of the lower support layer 134. In some embodiments, at least one rail 136 may be positioned at left side of the lower support layer 134. Particularly, the rails 136 may be provided on the upper surface 138 of the lower support layer 134. In some embodiments, the top wall 132 of the lower tray 106 may define the upper surface 138 to support the one or more rails 136. The rails 136 at the right side and the left side of the lower tray 106 may be aligned each other along the transverse axis 'T' of the jaw 100. In another embodiment, there may be more than one rails 136 at each of the right side and left side of the lower tray 106. Further, the number of rails 136 on the lower tray 106 may be equal to the number of indentation tracks 122 on the upper tray 104.

Figure 2:
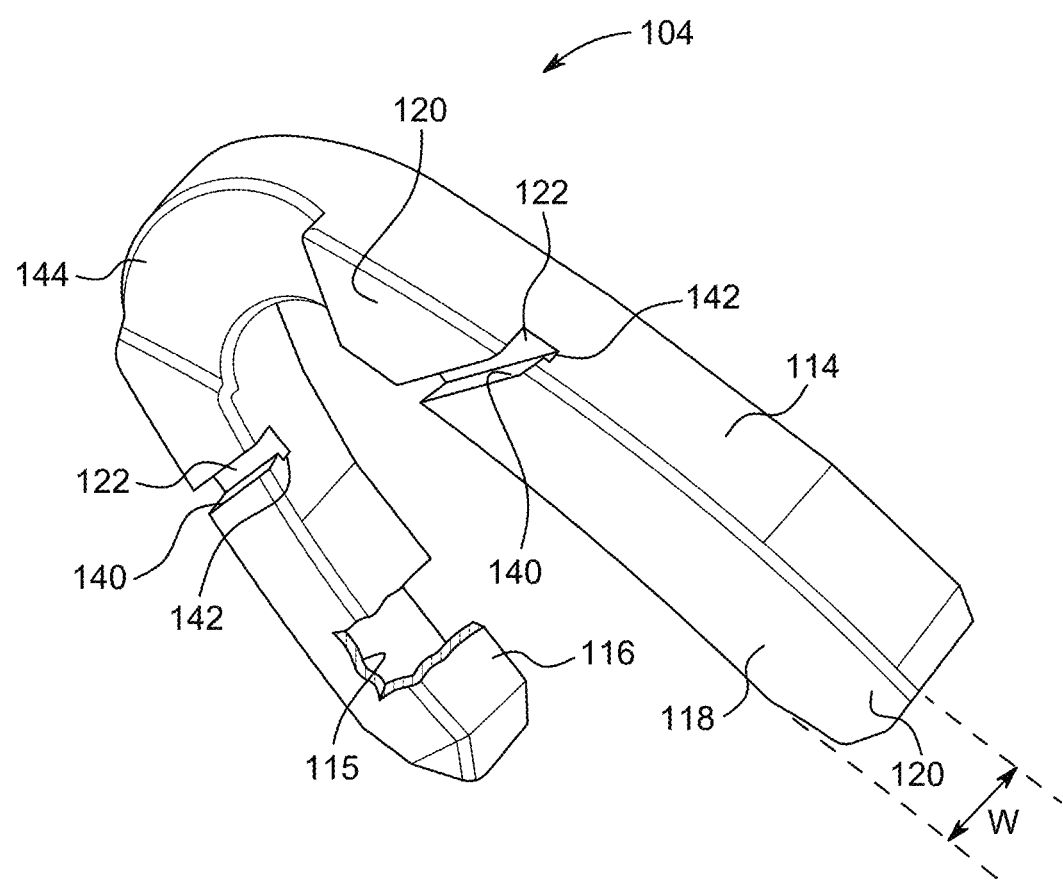
FIG. 2 illustrates a perspective view of the upper tray, according to an embodiment of the present disclosure.

Referring to FIG. 2, a perspective view of the upper tray 104 is illustrated, according to an embodiment of the present disclosure. The upper tray 104 includes the upper dentition-interfacing layer 115 and the upper support layer 120. A cut out portion is shown in the upper tray 104 only for the purpose of illustrating the upper dentition-interfacing layer 115. The one or more indentation tracks 122 in the upper support layer 120 may be defined as a groove. In some embodiments, the indentation track 122 may have an inverted L shape cross section. In such embodiments, the indentation track 122 includes a vertical groove portion 140 and a horizontal groove portion 142 extending radially towards the posterior of the jaw 100 from the vertical groove portion 140. In such embodiments, the vertical groove portion 140 and the horizontal groove portion 142 are together configured to movably receive the rail 136 provided in the lower support layer 134. In another embodiment, the horizontal groove portion 142 may extend radially towards anterior of the jaw 100 from the vertical groove portion 140. In some embodiments, the cross section of the indentation track 122 may be defined as a T shape. In such embodiments, the indentation track 122 includes a vertical groove portion 140 and two horizontal groove portions 142, one extending from the vertical groove portion toward the posterior of the jaw and the other extending from the vertical groove portion toward the anterior of the jaw. In some embodiments, the indentation track has a cross section resembling any other shape known in the art to movably receive the rail 136. The indentation track 122 may be provided throughout the entirety of a width 'W' of the upper support layer 120. In some embodiments, the indentation track 122 may be engraved on the bottom wall 118 of the upper tray 104.

In some embodiments, the one or more indentation tracks 122 provided in the upper support layer 120 are oriented in a substantially mediolateral direction, when the arch shape of the upper tray 104 is aligned with the upper dental arch 105. The mediolateral direction may be alternatively referred to as the transverse axis 'T' of the jaw 100.

In some embodiments, the upper tray 104 further comprises an air passage indentation 144 in order to support air inhalation when the upper tray 104 is fitted to the upper dentition 108 of the patient. The air passage indentation 144 is defined on the upper support layer 120 at a forward end of the upper tray 104. Particularly, the air passage indentation 144 may be defined at the bottom wall 118 of the upper tray 104. Dimensional characteristics such as a width and a length of the spacious structure 144 may be defined based on the additional breathing support required while the patient is sleeping. In some embodiments, the adjustable dental appliance further comprises one or more air passage inserts. The air passage insert allows the user to partially or totally occlude the air passage indentation 144. In some embodiments, the air passage inserts are removably inserted into the air passage indentation. In general, the air passage insert may be secured to the upper tray using any suitable attachment mechanism known to one of ordinary skill in the art. Examples of such attachment mechanisms include, but are not limited to magnetic mechanisms, press-fit mechanisms, snap-fit mechanisms, clip-in mechanisms, slide-in mechanisms, rail and groove mechanisms, and adhesive mechanisms.

In some embodiments, the upper tray 104 may be manufactured using any suitable method known to one of ordinary skill in the art. In some embodiments, the upper tray 104 is constructed using a 3D printing method. In some embodiments, the upper tray 104 is constructed using a milling method, for example CNC milling. In some embodiments, the upper tray 104 is constructed using a molding method, for example injection molding. In some embodiments, the upper tray 104 is constructed using a combination of methods, with different method being used for different portions of the upper tray. In such embodiments, the upper support layer may be constructed using a first method and the upper dentition-interfacing layer may be constructed using a second method. In certain embodiments, the upper tray 104 is configured to encompass at least a portion of the upper dentition 108. In one such embodiment, the upper tray 104 may encompass till a first molar tooth or premolar teeth of the upper dentition 108. In another such embodiment, the upper tray 104 may encompass till a third molar tooth of the upper dentition 108. The size and shape of the upper dentition-interfacing layer 115 and the upper support layer 120 of the upper tray 104 may be defined based on the size and shape of the upper dentition 108. In some embodiments, the upper dentition-interfacing layer 115 conforms to the upper dentition 108. In some embodiments, the upper dentition-interfacing layer 115 is molded to conform to the upper dentition 108. In such embodiments, the upper dentition-interfacing layer 115 may be molded before the upper dentition-interfacing layer 115 is attached to, disposed upon, connected with, or otherwise integrated into the other components of the upper tray 104. In alternative such embodiments, the upper dentition-interfacing layer 115 may be molded after the upper dentition-interfacing layer 115 is attached to, disposed upon, connected with, or otherwise integrated into the other components of the upper tray 104. In some embodiments, the upper dentition-interfacing layer 115 is milled to conform to the upper dentition 108.

Figure 3:
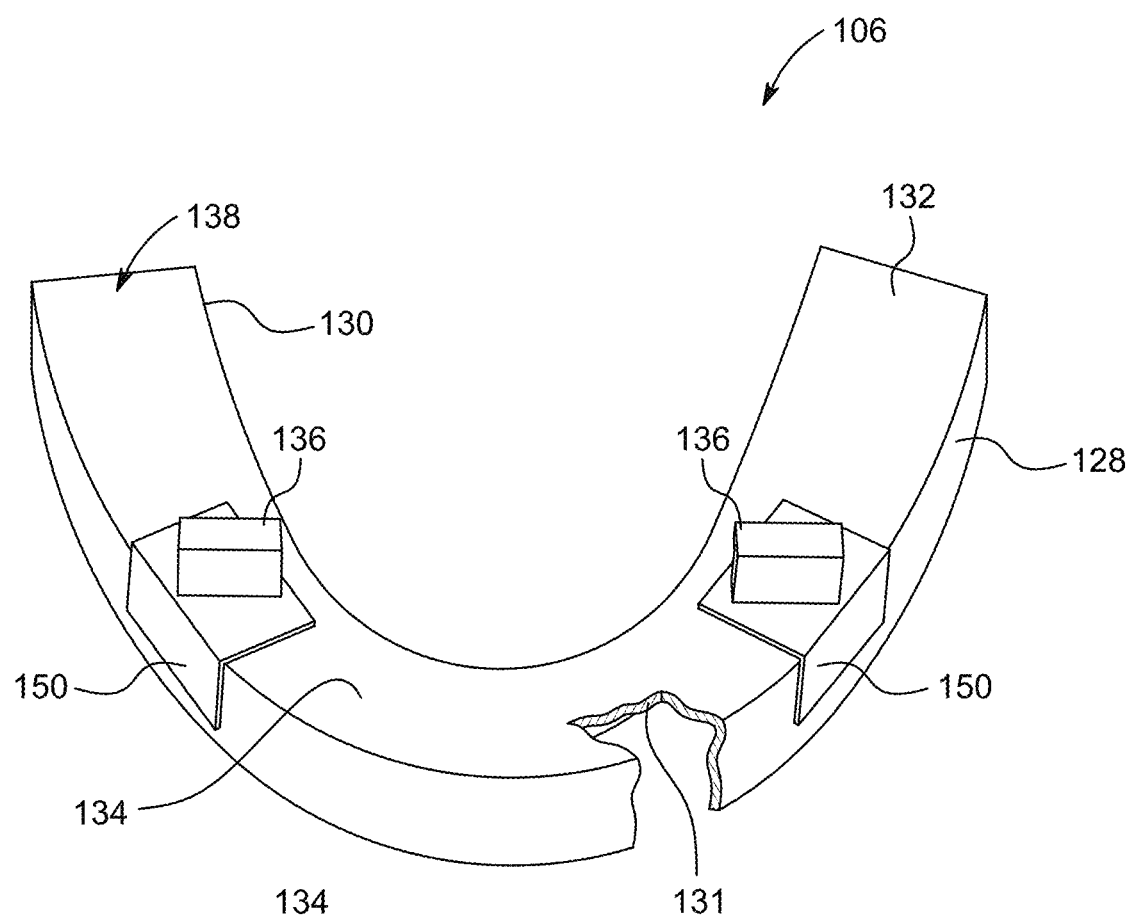
FIG. 3 illustrates a perspective view of the lower tray, according to an embodiment of the present disclosure.

Referring to FIG. 3, a perspective view of the lower tray 106 is illustrated, according to an embodiment of the present disclosure. The lower tray 106 includes the lower dentition-interfacing layer 131 and the lower support layer 134. A cut out portion is shown in the lower tray 106 only for the mere purpose of illustrating the lower dentition-interfacing layer 131. The lower support layer 134 includes the one or more rails 136 attached to the upper surface 138 of the lower support layer 134. In some embodiments, lower tray further comprises a support member 150. In some embodiments, the one or more rails 136 are attached to the support member 150. In some embodiments, the support member 150 is immovably attached to, disposed upon, connected with, or otherwise integrated into the lower support layer 134. In alternative embodiments, the support member 150 is reversibly attached, secured, or fastened to the lower support layer 134. In general, this reversible attachment, securing, or fastening may be achieved using any suitable method or device known to one of ordinary skill in the art. In some embodiments, the support member 150 is reversibly attached, secured, or fastened to the lower support layer 134 using screws. In some embodiments, the support member 150 is reversibly attached, secured, or fastened to the lower support layer 134 using a snap-fit mechanism. In some embodiments, lower support layer 134 comprises a plurality of support member attachment points to which the support member 150 is reversibly attached, secured, or fastened. In such embodiments, the support member 150 is reversibly attached, secured, or fastened to one or more of the support member attachment points. The plurality of support member attachment points allow the position and/or orientation of the support member 150 to be adjusted relative to the lower support layer 134. The support member 150 may be attached symmetrically on both the right side and left side of the lower support layer 134. In some embodiments, the support member 150 may be disposed over the upper surface 138 of the lower support layer 134. In some embodiments, the support member 150 is located above the premolar tooth or the incisor tooth. In alternative embodiments, the support member 150 is disposed at other locations on the lower support layer 134. In general, the support member 150 may be constructed of any suitable material known to one of ordinary skill in the art. In some embodiments, the support member 150 is made of a non-toxic metal. In alternative embodiments, the support member 150 is made of materials such as plastic, polymer or any non-toxic non-metal.

Similar to the orientation of the indentation tracks 122 in the upper tray described in FIG. 2, the one or more rails 136 may also be oriented in the mediolateral direction, when the arch shape of the lower tray 106 is aligned with the lower dental arch 107. The mediolateral direction may be alternatively referred to as the transverse axis 'T' of the jaw 100.

The lower tray 106 may be manufactured as described above. In some embodiments, the lower tray 106 may be configured to encompass at least a portion of the lower dentition 112. In one such embodiment, the lower tray 106 may encompass till the first molar tooth or the premolar teeth of the lower dentition 112. In another such embodiment, the lower tray 106 may encompass till the third molar tooth of the lower dentition 112. The size and shape of the lower dentition-interfacing layer 131 and the lower support layer 134 may be defined based on the size and shape of the lower dentition 112. In some embodiments, the lower dentition-interfacing layer 131 conforms to the lower dentition 112. In some embodiments, the lower dentition-interfacing layer 131 is molded to conform to the lower dentition 112. In such embodiments, the lower dentition-interfacing layer 131 may be molded before the lower dentition-interfacing layer 131 is attached to, disposed upon, connected with, or otherwise integrated into the other components of the lower tray 106. In alternative such embodiments, the lower dentition-interfacing layer 131 may be molded after the lower dentition-interfacing layer 131 is attached to, disposed upon, connected with, or otherwise integrated into the other components of the lower tray 106. In some embodiments, the lower dentition-interfacing layer 131 is milled to conform to the lower dentition 112.

Figure 4:
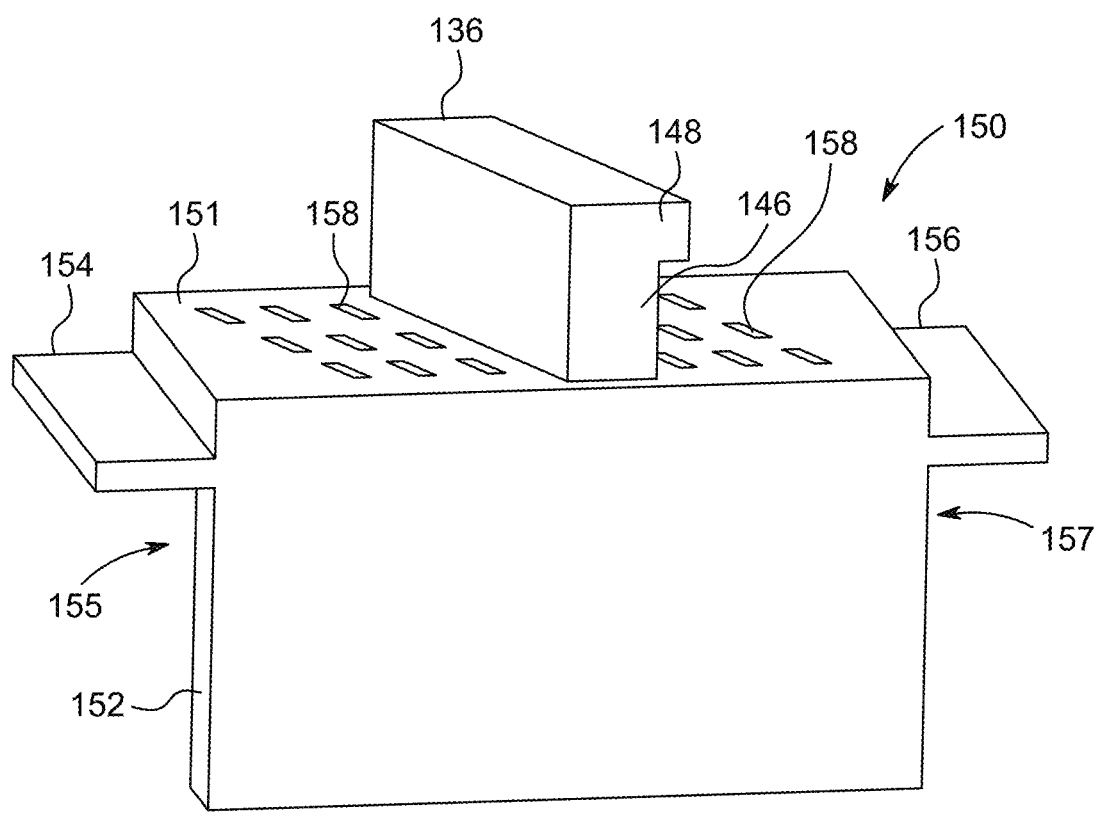
FIG. 4 illustrates an enlarged view of a rail affixed on the lower tray, according to an embodiment of the present disclosure.

Referring to FIG. 4, an enlarged view of the rail 136 and the support member 150 is illustrated, according to an embodiment of the present disclosure. The rail 136 may be removably and movably attached to the lower support layer. In some embodiments, the rail 136 is removably and movably attached to the support member 150. The support member 150 may be disposed over the upper surface 138 of the lower support layer 134. In some embodiments, the rail 136 includes a vertical extension 146 and a horizontal extension 148 extending from the vertical extension 146. The vertical extension 146 and the horizontal extension 148 are together configured to define an inverted L shape cross section to movably receive within the indentation track 122. In such embodiments, the vertical extension 146 and the horizontal extension 148 are movably received within the vertical groove portion 140 and the horizontal groove portion 142, respectively, of the indentation track 122. The vertical extension 146 of the rail 136 is movably attached to the support member 150 as such the rail 136 may move forward or backward with respect to the support member 150. In some embodiments, the rail 136 may have a 'T' shape or other shapes adapted to engage with the corresponding shape of the indentation track 122 of the upper tray 104. In some embodiments, the rail 136 is removably and movably attached to the support member 150 and/or the lower support layer 134 by screws. In some embodiments, the rail 136 is removably and movably attached to the support member 150 and/or the lower support layer 134 by a snap-fit mechanism. In general, the rail 136 may be constructed of any suitable material known to one of ordinary skill in the art. In some embodiments, the rail 136 is made of a non-toxic metal. In alternative embodiments, the rail 136 is made of materials such as plastic, polymer or any non-toxic non-metal. The plastic, polymer, or non-toxic non-metal may be rigid or flexible. In some embodiments, the rail 136 is flexible, allowing limited protrusion/retraction and/or elevation/depression motion of a jaw fitted with the adjustable dental appliance. In such embodiments, the rail 136 should not be so flexible as to allow the rail 136 to easily be dislodged from the indentation track or inhibit the device from remaining in an interlocked configuration.

In some embodiments, the support member 150 may include an upper platform 151 and a side wall 152 which together define an inverted L shape. In some embodiments, the upper platform 150 is configured to attach with the upper surface 138 of the lower support layer 134 and/or the side wall 152 is configured to attach with the outer side wall 128 of the lower tray 106. In some embodiments, the side wall 152 of the support member 150 may be attached to the inner side wall 130 of the lower tray 106. In some embodiments, the plurality of support member attachment points are located on any combination of the upper surface 138 of the lower support layer, the inner side wall 130 of the lower tray 106, and the outer side wall 128 of the lower tray 106. In some embodiments, the support member 150 is reversibly attached, secured, or fastened to any combination of the upper surface 138 of the lower support layer, the inner side wall 130 of the lower tray 106, and the outer side wall 128 of the lower tray. In some embodiments, the support member 150 further includes a first protrusion 154 at a forward end 155 of the support member 150 and/or a second protrusion 156 at a backward end 157 of the support member 150. The first protrusion 154 and/or the second protrusion 156 may be configured to facilitate attachment of the support member 150 with the lower tray 106. The first protrusion 154 and/or the second protrusion 156 may serve to increase the rigidity or other structural integrity of the support member 150. In some embodiments, the first protrusion 154 and the second protrusion 156 are rigidly attached with the top wall 132 of the lower tray 106. In some embodiments, the support member 150 comprises a support member height adjustment mechanism. The height adjustment mechanism is capable of adjusting a height of the support member, the height being measured in a direction nominally perpendicular to an occlusal surface of the lower dentition. In general, any suitable height adjustment mechanism known to one of ordinary skill in the art may be used. In some embodiments, the height adjustment mechanism comprises a plurality of support member attachment points on the inner side wall 130 of the lower tray 106 and/or the outer side wall 128 of the lower tray 106. In some embodiments, the support member height adjustment mechanism comprises support member height spacers placed between the support member 150 and the upper surface 138 of the lower support layer. In some embodiments, the support member height spacers are washers. In some embodiments, the support member height adjustment mechanism comprises height-adjusting screws. In some embodiments, the support member 150 comprises a support member tilt adjustment mechanism. The tilt adjustment mechanism is capable of adjusting a roll tilt (rotation of the support member about its center about an axis parallel to the L axis in FIG. 1) and/or a pitch tilt (rotation of the support member about its center about an axis parallel to the T axis in FIG. 1) of the support member 150. In general, any suitable tilt adjustment mechanism known to one of ordinary skill in the art may be used. In some embodiments, the support member tilt adjustment mechanism comprises support member tilt spacers placed between the support member 150 and the upper surface 138 of the lower support layer. In some embodiments, the support member tilt spacers are the same spacers as the support member height spacers. In some embodiments, the support member tilt adjustment mechanism comprises tilt-adjusting crews. In some embodiments, the tilt-adjusting screws are the same as the height-adjusting screws.

In some embodiments, the lower tray 106 further comprises an array of attachment points 158 to which the one or more rails 136 are affixed. In some embodiments, the array of attachment points 158 is attached to, disposed upon, formed from, or otherwise integrated with the lower tray 106. In some embodiments, the array of attachment points 158 is attached to, disposed upon, formed from, or otherwise integrated with the lower support layer 134. In some embodiments, the array of attachment points 158 is attached to, disposed upon, formed from, or otherwise integrated with the support member 150. The array of attachment points 158 allow adjustment of the positioning of the one or more rails 136. In some embodiments, the array of attachment points 158 allows the position of the one or more rails 136 to be adjusted over the lower tray 106, such that the rails 136 may be adjusted either forward or backward on the lower tray 106. In some embodiments, adjustment of the position of the one or more rails 136 adjusts a protrusive orientation 'P' (shown in FIG. 5B) of the lower jaw 110 with respect to the upper jaw 109 of the patient. In some embodiments, the array of attachment points 158 allows the position of the one or more rails 136 to be adjusted based on a desired protrusive orientation.

A schematic representation of the array of attachment points 158 is shown on the upper platform 151 of the support member 150. In some embodiments, the array of attachment points 158 may be a pattern of multiple protrusions extending from the upper platform 151 of the support member 150. In another embodiment, the array of attachment points 158 may be a pattern of multiple engraved portions in the upper platform 151 of the support member 150. In some embodiments, each attachment points 158 has a spacing from adjacent attachment points 158 of 0.5 to 2.0 mm, preferably 0.55 to 1.95 mm, preferably 0.60 to 1.90 mm, preferably 0.65 to 1.85 mm, preferably 0.70 to 1.80 mm, preferably 0.75 to 1.85 mm, preferably 0.80 to 1.70 mm, preferably 0.85 to 1.65 mm, preferably 0.9 to 1.6 mm, preferably 0.95 to 1.55 mm, preferably 1.00 to 1.50 mm along a length of the array of attachment points. In such embodiments, the rail 136 may be adjusted over the array of attachment points in a forward or backward direction in increments of about 0.5 mm to 2.0 mm, preferably 0.55 to 1.95 mm, preferably 0.60 to 1.90 mm, preferably 0.65 to 1.85 mm, preferably 0.70 to 1.80 mm, preferably 0.75 to 1.85 mm, preferably 0.80 to 1.70 mm, preferably 0.85 to 1.65 mm, preferably 0.9 to 1.6 mm, preferably 0.95 to 1.55 mm, preferably 1.00 to 1.50 mm.

The spacing between the two adjacent attachment points 158 over the array of attachment points may be defined based on the desired protrusive orientation 'P' of the lower dental arch 107 with respect to the upper dental arch 105. Accordingly, the rail 136 may be affixed to the attachment points 158 over the lower tray 106 based on the desired protrusive orientation 'P' of the lower dental arch 107. The adjustable dental appliance 102 of the present disclosure thus provides adjustment of the protrusive orientation 'P' of the lower dental arch 107 with respect to the upper dental arch 105 of the patient over a total length of the array of attachment points. In some embodiments, the array of attachment points has a total length of 2.5 to 15 mm, preferably 2.75 to 12.5 mm, preferably 3 to 12 mm, preferably 3.5 to 11 mm, preferably 4 to 10 mm, preferably 4.5 to 7.5 mm. (shown in FIG. 5B). In such embodiments, the array of attachment points 158 allows for adjustment of the protrusive orientation 'P' of the lower dental arch 107 with respect to the upper dental arch 105 of the patient fitted with the adjustable dental appliance 102 by 2.5 to 15 mm preferably 2.75 to 12.5 mm, preferably 3 to 12 mm, preferably 3.5 to 11 mm, preferably 4 to 10 mm, preferably 4.5 to 7.5 mm. The adjustment range of the protrusive orientation 'P' of the lower dental arch 107 may vary depending upon the spacing between the attachment points 158 on the upper platform 151 of the support member 150 and the total length of the array of attachment points.

In some embodiments, the lower tray 106 comprises a rail height adjustment mechanism. The rail height adjustment mechanism is capable of adjusting a height of the rail or rails 136 attached to the lower tray 106, the height being measured in a direction nominally perpendicular to an occlusal surface of the lower dentition. In general, any suitable rail height adjustment mechanism known to one of ordinary skill in the art may be used. In some embodiments, the rail height adjustment mechanism comprises rail height spacers. In some embodiments, the rail height spacers are placed between the rail or rails 136 and the upper surface 138 of the lower support layer and/or between the rail or rails 136 and the support member 150. In some embodiments, the rail height spacers are washers. In some embodiments, the rail height adjustment mechanism comprises rail height-adjusting screws. In some embodiments, the lower tray 106 comprises a rail tilt adjustment mechanism. The rail tilt adjustment mechanism is capable of adjusting a roll tilt (rotation of the rail about its center about an axis parallel to the L axis in FIG. 1) and/or a pitch tilt (rotation of the rail about its center about an axis parallel to the T axis in FIG. 1) of the rail 136. In general, any suitable tilt adjustment mechanism known to one of ordinary skill in the art may be used. In some embodiments, the rail tilt adjustment mechanism comprises rail tilt spacers. In some embodiments, the rail tilt spacers are placed between the rail 136 and the upper surface 138 of the lower support layer and/or between the rail 136 and the support member 150. In some embodiments, the rail tilt spacers are the same spacers as the rail height spacers. In some embodiments, the rail tilt adjustment mechanism comprises rail tilt-adjusting screws. In some embodiments, the rail tilt-adjusting screws are the same as the rail height-adjusting screws. In some embodiments, the rail height adjustment mechanism and/or the rail tilt adjustment mechanism is part of the support member 150.

In some embodiments, the adjustable dental appliance further comprises a shock absorbing mechanism. In some embodiments, the shock absorbing mechanism is part of the support member height adjustment mechanism, the support member tilt adjustment mechanism, the rail height adjustment mechanism, the rail tilt adjustment mechanism, or any combination thereof. In some embodiments, the shock absorbing mechanism comprises any or all of the support member height spacers, the support member tilt spacers, the rail height spacers, and the rail tilt spacers (collectively, "the spacers"). In some such embodiments, the spacers are springs. In alternative such embodiments, the spacers are made of a shock absorbing material. The shock absorbing material may be any suitable material known to one of ordinary skill in the art. Examples of such shock absorbing material include, but are not limited to, polyurethanes, silicones, butyl rubbers, neoprene rubbers, and polyolefins. The shock absorbing material may take any suitable form known to one of ordinary skill in the art. Examples of such forms include, but are not limited to a solid, a foam, a gel, and an encapsulated liquid. In some embodiments, the shock absorbing mechanism allows for a change in height of the support member and/or the rail. In some embodiments, the change in height results in a compressed height of the support member and/or the rail, the compressed height being smaller than an uncompressed height of the support member and/or the rail. In such embodiments, the shock absorbing mechanism allows for a compressed height of the support member and/or the rail of no less than 75% of the uncompressed height of the support member and/or the rail, preferably no less than 80%, preferably no less than 85%, preferably no less than 90%, preferably no less than 95% of the uncompressed height of the support member and/or the rail. In some embodiments, the shock absorbing mechanism allows for a change in tilt of the support member and/or the rail. In some embodiments, the change in tilt results in a compressed tilt of the support member and/or the rail, the compressed tilt being either greater than or less than an uncompressed tilt of the support member and/or the rail. In such embodiments, the shock absorbing mechanism allows for a compressed tilt of the support member and/or the rail which differs from the uncompressed tilt by no more than 25% of the uncompressed tilt of the support member and/or the rail, preferably no more than 20%, preferably no more than 15%, preferably no more than 10%, preferably no more than 5% of the uncompressed tilt of the support member and/or the rail. The reduction in height and/or the change in tilt afforded to the support member 150 and/or the rail or rails 136 by the shock absorbing mechanism may impart greater freedom of movement of a jaw fitted with the device. In some embodiments, the shock absorbing mechanism is a part of the one or more indentation tracks 122 and/or the one or more rails 136. In some such embodiments, the shock absorbing mechanism comprises a shock absorbing pad or coating attached to or disposed upon the one or more indentation tracks 122 and/or the one or more rails 136. In such embodiments, the shock absorbing pad or coating is made of a shock absorbing material as described above. Additionally, the shock absorbing mechanism may cushion impacts, clenching, or grinding of a jaw fitted with the device. The greater freedom of movement and/or the cushioning may increase the comfort of a patient fitted with the device.

In some embodiments, the upper dentition-interfacing layer 115 of the upper tray 104 and/or the lower dentition-interfacing layer 131 of the lower tray 106 are made of a biocompatible polymer. The biocompatible polymer in general may be any suitable polymer known to one of ordinary skill in the art, but should be selected so as to not cause any adverse reaction or toxicity between the adjustable dental appliance 102 and the skin nearby interfacing area of the upper dentition 108 and the lower dentition 112 of the patient. In some embodiments, the biocompatible polymer is at least one selected from the group consisting of a nylon, a polyolefin, a polyolefin-vinyl acetate copolymer, and a polyacrylate.

Referring to FIG. 5A, an interlocked configuration of the adjustable dental appliance 102 is illustrated, according to an embodiment of the present disclosure. More specifically, a neutral position of the adjustable dental appliance 102 is shown in FIG. 5A. This neutral position refers to a position in which the protrusive orientation of the patient's jaw fitted with the device is substantially the same as the protrusive orientation of the patient's jaw without the device present. The one or more rails 136 of the lower tray 106 fit securely into the one or more indentation tracks 122 of the upper tray 104 and thereby interlocking the upper tray 104 and the lower tray 106. In some embodiments, the one or more indentation tracks 122 in the upper tray 104 are larger or wider than the one or more rails 136. Such an increase in size or width may be necessary or advantageous in order to allow the rails 136 to enter and run freely within the indentation tracks 122 in the mediolateral direction. In such embodiments, the increase in size or width should not be so great as to allow the one or more rails to inadvertently leave the one or more indentation tracks, thereby de-interlocking the device. In some embodiments, the one or more indentation tracks 122 in the upper tray 104 are 0.5 mm wider than the one or more rails 136.

At the neutral position of the adjustable dental appliance 102, the rails 136 may be attached on the array of attachment points 158 at a center of the array of attachment points. In some embodiments, the center of the array of attachment points may be located at a position that corresponds to a center of the lower tray 106. In an interlocked configuration, the one or more rails 136 of the lower tray 106 are securely fitted within the one or more indentation tracks 122 of the upper tray 104. In some embodiments, the rails 136 may only enter or exit the corresponding indentation tracks 122 either from the right track end 121 or the left track end 123 of the upper tray 104. At the neutral position of the adjustable dental appliance 102, the rails 136 of the lower tray 106 and the indentation tracks 122 of the upper tray 104 are interlocked such that the upper dental arch 105 and the lower dental arch 107 are aligned each other in substantially the same manner that the upper dental arch 105 and the lower dental arch 107 are aligned with each other in the absence of the device. Particularly, no change in protrusive orientation of the lower dental arch 107 is achieved with respect to the upper dental arch 105. In alternative embodiments, the upper tray 104 and lower tray 106 are interlocked in a non-neutral position. The non-neutral position is one in which the upper dental arch 105 and the lower dental arch 107 are not aligned each other in substantially the same manner that the upper dental arch 105 and the lower dental arch 107 are aligned with each other in the absence of the device. Such a position may be referred to as an adjusted position.

In some embodiments, when the upper tray 104 and the lower tray 106 are interlocked by securely fitting the one or more rails 136 into the one or more indentation tracks 122, the one or more rails 136 can move along a length of the one or more indentation tracks 122. Such motion may allow for substantial motion of the upper tray with respect to the lower tray in the mediolateral direction. In some embodiments, the length of the indentation track 122 is equal to the width 'W' of the upper tray 104. In some embodiments, when the upper tray 104 and the lower tray 106 are interlocked by securely fitting the one or more rails 136 into the one or more indentation tracks 122, the jaw 100 fitted with the adjustable dental appliance 102 is permitted to move in a side-to-side motion. In some embodiments, the jaw 100 fitted with the adjustable dental appliance 102 in an interlocked configuration is inhibited from depression/elevation jaw motions and/or protrusion/retraction jaw motions.

Referring to FIG. 5B, an interlocked configuration of the adjustable dental appliance 102 is illustrated, according to an embodiment of the present disclosure. More specifically, an adjusted position of the adjustable dental appliance 102 is shown in FIG. 5B. In some embodiments, the rails 136 may be attached on the array of attachment points 158 at 1 mm behind the center of the upper platform 151 of the support member 150. Particularly, the rails 136 may be moved from the neutral position by 1 mm towards the posterior of the jaw 100. Such position of the rail 136 on the lower tray 106 may be referred as '+1 position' of the rail 136 with respect to the support member 150. At the +1 position, the rails 136 of the lower tray 106 fit securely into the indentation tracks 122 of the upper tray 104 and thereby interlocking the upper tray 104 and the lower tray 106 such that the lower dental arch 107 moves forward relative to the upper dental arch 105 by 1 mm from a neutral position. Thereby a change of the protrusive orientation of 1 mm is achieved between the lower dental arch 107 and the upper dental arch 105.

In another embodiment, the rails 136 may be attached on the array of attachment points 158 at 2 mm behind the center of the upper platform 151 of the support member 150. Particularly, the rails 136 may be moved from the neutral position by 2 mm towards the posterior of the jaw 100. Such position of the rails 136 on the lower tray 106 may be referred as '+2 position' of the rails 136 with respect to the support member 150. At the +2 position, the rails 136 of the lower tray 106 fit securely into the indentation tracks 122 of the upper tray 104 and thereby interlocking the upper tray 104 and the lower tray 106 such that the lower dental arch 107 moves forward relative to the upper dental arch 105 by 2 mm from a neutral position. Thereby a change of the protrusive orientation of 2 mm is achieved between the lower dental arch 107 and the upper dental arch 105. Similarly, the rails 136 may be attached on the array of attachment points 158 at 3 mm behind the center of the upper platform 150 of the support member 150 to achieve a change of the protrusive orientation of 3 mm between the lower dental arch 107 and the upper dental arch 107. Also, the rails 136 may be attached on the array of attachment points 158 at 4 mm behind the center of the upper platform 150 of the support member 150 to achieve a change of the protrusive orientation of 4 mm between the lower dental arch 107 and the upper dental arch 105.

In certain conditions or as per the comfort of the patient, the rails 136 may be attached on the array of attachment points 158 at 1 mm ahead of the center of the upper platform 150 of the support member 150. Such position of the rails 136 on the lower tray 106 may be referred as '−1 position' of the rails 136 with respect to the support member 150. At the −1 position, the rails 136 of the lower tray 106 fit securely into the indentation tracks 122 of the upper tray 104 and thereby interlocking the upper tray 104 and the lower tray 106 such that the lower dental arch 107 moves backward relative to the upper dental arch 105 by 1 mm from a neutral position.

In various embodiments, initial mandibular protrusion position may be 50% of maximum mandibular protrusion with the average maximum protrusion being about 10 mm. However, in some embodiments, the mandibular protrusion may reach up to 90% of the maximum mandibular protrusion depending on the need of patients. Also, as per the comfort level of the patient, mandibular advancement may be adjusted backward to 40%, 30% or 20% to maximize patient's comfort.

Figure 6:
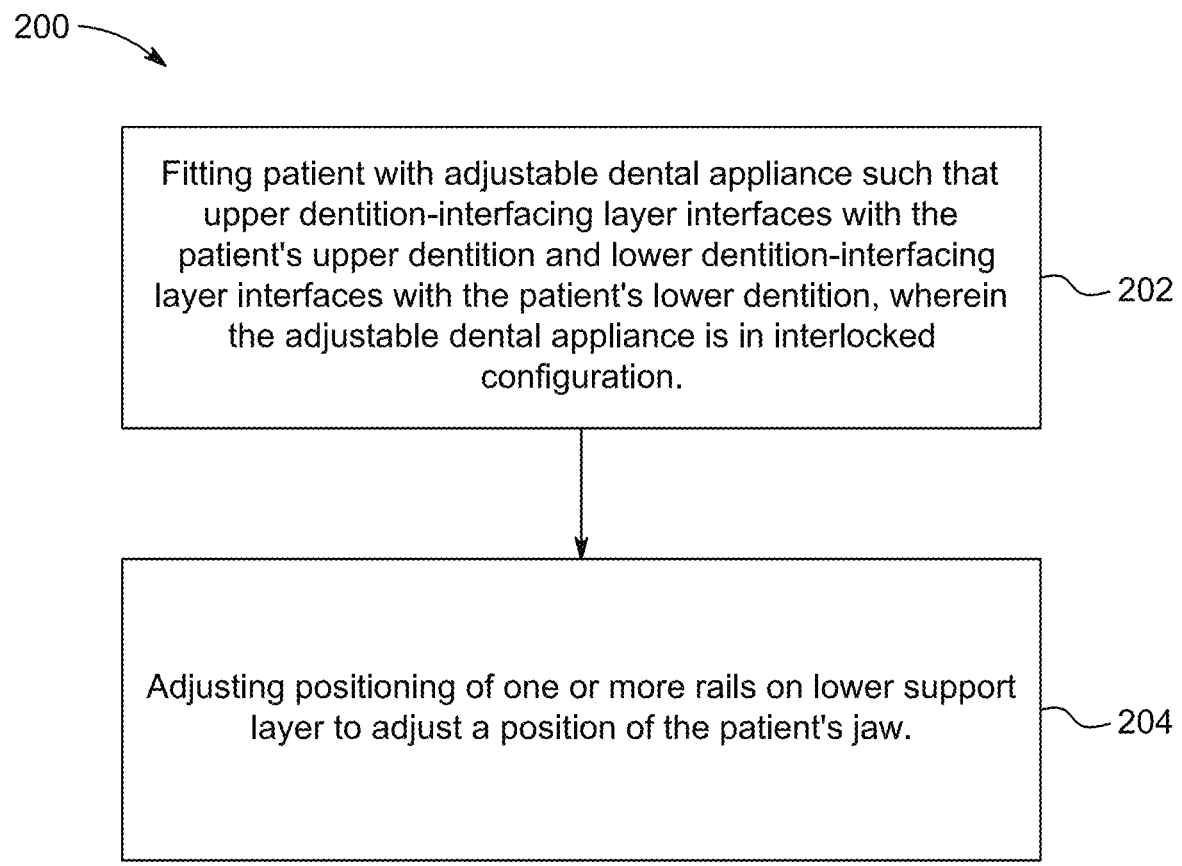
FIG. 6 illustrates a method of treating obstructive sleep apnea and snoring using the adjustable dental appliance, according to an embodiment of the present disclosure.

Referring to FIG. 6, methods 200 of treating obstructive sleep apnea and snoring using the adjustable dental appliance 102 are illustrated, according to various embodiments of the present disclosure. The methods 200 of treating obstructive sleep apnea and snoring using the adjustable dental appliance 102 are described with reference to the FIGS. 1 through 5B. At step 202, the methods 200 include fitting the patient with the adjustable dental appliance 102 such that the upper dentition-interfacing layer 115 interfaces with the patient's upper dentition 108 and the lower dentition-interfacing layer 131 interfaces with the patient's lower dentition 112. At step 204, the methods 200 further comprise adjusting the positioning of the rails 136 on the lower support layer 134 to adjust the position of the patient's jaw 100. In some embodiments, the rails 136 may be adjusted such that the jaw is in a neutral position or a non-neutral position as described above. In such embodiments, the rails are adjusted so as to achieve a desired protrusive orientation of the jaw fitted with the device. After adjusting the position of the rails 136 on the support member 150, the rails 136 of the lower tray 106 fit securely into the indentation tracks 122 of the upper tray 104, thereby interlocking the upper tray 104 with the lower tray 106. In some embodiments, the interlocking is performed by first aligning the indentation tracks 122 and the rails 136 coaxially in the mediolateral direction, then sliding the rails 136 into the indentation tracks 122 of the upper tray 104 from either the left track end 123 or from the right track end 121 such that the rails 136 move along the length of the indentation tracks 122. In such embodiments, both the rails 136 at either side of the longitudinal axis 1' are simultaneously inserted into both the indentation tracks 122. In some embodiments, as the indentation tracks 122 are unobstructed, the rails 136 passes through the entirety of the length of the indentation tracks 122 and enter or exit the indentation tracks 122 via the left track end 123 or the right track end 121. For example, the rails 136 may enter the indentation tracks 122 either from the left track end 123 or the right track end 121, and thereby permitting the patient to have a freedom to begin the interlocking process by entering the rails 136 into the indentation tracks 122 from either the left track end 123 or the right track end 121. In the interlock configuration, the rails 136 securely fit within the indentation tracks 122 on either side of the jaw 100 of the patient.

After the upper tray 104 and the lower tray 106 of the adjustable dental appliance 102 are interlocked, the adjustable dental appliance 102 is received within the mouth of the patient. As the upper dentition-interfacing layer 115 of the upper tray 104 interfaces with the upper dentition 108 of the upper jaw 109 and the lower dentition-interfacing layer 131 of the lower tray 106 interfaces with the lower dentition 112 of the lower jaw 110, the adjustable dental appliance 102 is securely seated within the mouth of the patient. In some embodiments, the upper jaw 109 and the lower jaw 110 are positioned in the interlock configuration such that the jaw 100 fitted with the adjustable dental appliance 102 is permitted to move in the side-to-side motion as the rails 136 can slide freely within the indentation tracks 122. In some embodiments, in the interlock configuration, the lower jaw 110 is inhibited from depression/elevation jaw motions and/or protrusion/retraction jaw motions. In some embodiments, the horizontal extension 148 of the rail 136 is engaged with the horizontal groove portion 142 of the indentation track 122, such that the depression/elevation jaw motion of the jaw 100 is inhibited. In some embodiments, the vertical extension 146 of the rail 136 is engaged with the vertical groove portion 140 of the indentation track 122, such that the protrusion/retraction jaw motion of the jaw 100 is inhibited. In such embodiments, the patient wearing the adjustable dental appliance 102 can have the side-to-side motion of the jaw 100 whereas the vertical, forward or backward movements of the lower jaw 110 are restricted. Accordingly, the lateral movement of the lower dental arch 107 with respect to the upper dental arch 105 solves the problem of bruxism. In some embodiments, when the patient wears the adjustable dental appliance 102, the jaw 100 of the patient is positioned in such a way to alleviate or prevent airway obstruction. In some embodiments, adjusting the position of the rails 136 on the lower support layer 134 helps to adjust the position of the patient's lower jaw 110 with respect to the upper jaw 109, thereby alleviating or preventing the airway obstruction and solving the problem of obstructive sleep apnea and snoring.

Various, embodiments, examples and dimension of the components used in the disclosure are merely exemplary. Any person skilled in the relevant art may perform numerous modifications and variations of the present disclosure such as shape, size, position or orientation of the components such as tracks, rails, groves or attachment points involved in the invention in light of the above teachings. It is therefore to be understood that within the scope of the appended claims, the invention may be practiced otherwise than as specifically described herein.

The invention claimed is:

1. A sleep apnea treatment system, comprising:
   an upper jaw piece having an upper tooth side and an opposing upper support side, the upper jaw piece having an arch shape and the upper support side having two indentation tracks oriented in a substantially mediolateral direction across the width of the upper jaw piece when the arch shape of the upper jaw piece is aligned with an upper dental arch; the upper jaw piece further having an air passage indentation at a forward end across the width of the upper jaw piece, and wherein the upper support side of the upper jaw piece is flat, and
   a lower jaw piece having a lower tooth side and an opposing lower support side, the lower jaw piece having an arch shape and the lower support side having two rails reversibly attached to support members that are reversibly attached to an upper surface of the lower support side such that the two rails are oriented in a substantially mediolateral direction on opposing sides of the lower jaw piece when the arch shape of the lower jaw piece is aligned with a lower dental arch, wherein the two rails are the only rails projecting from the upper surface of the lower support side of the lower jaw piece, wherein the support members are immovably attached to the upper surface of the lower support side and each has an array of attachment points to which the rails are reversibly affixed, said arrays configured to adjust the positioning of the rails on the lower support side, wherein the lower jaw piece and the upper jaw piece are not connected and at least the upper jaw piece is injection molded, wherein the arch shapes of the lower jaw piece and the upper jaw piece are symmetrical about a longitudinal axis L and wherein the two rails of the lower jaw piece and the two indentation tracks of the upper jaw piece are parallel with a transverse axis T that is perpendicular to the longitudinal axis L, wherein the two rails of the lower jaw piece have a width that is less than a width of the two indentation tracks of the upper jaw piece and fit into the two indentation tracks of the upper jaw piece, thereby fitting the upper jaw piece and the lower jaw piece to permit contact between the upper support side of the upper jaw piece and the lower support side of the lower jaw piece, wherein each of the two rails has a vertical extension connected to the upper surface of the lower support side of the lower jaw piece and a horizontal extension connected to a top of the vertical extension, wherein the vertical extension and the horizontal extension define an inverted L shape cross section having a planar front face that faces forward toward an apex of the arch shape and a back face facing rearward toward ends of the arch shape, wherein the horizontal extension extends rearward from the back face, wherein the indentation tracks are unobstructed, permitting the rails to pass through the entirety of the length of the indentation tracks and enter or exit the indentation tracks via a left track end and a right track end, wherein each of the indentation tracks has a vertical groove portion and a horizontal groove portion to movably receive the vertical extension and the horizontal extension, respectively.

2. The sleep apnea treatment system of claim 1, wherein the rails of the lower jaw piece fit securely into the indentation tracks of the upper jaw piece such that the rails can move along a length of the indentation tracks.

3. The sleep apnea treatment system of claim 1, wherein the rails of the lower jaw piece fit securely into the indentation tracks of the upper jaw piece such that a jaw fitted with the upper jaw piece and the lower jaw piece is permitted to move in a side-to-side motion.

4. The sleep apnea treatment system of claim 1, wherein the rails of the lower jaw piece fit securely into the indentation tracks of the upper jaw piece such that a jaw fitted with the upper jaw piece and the lower jaw piece is inhibited from depression/elevation jaw motions and/or protrusion/retraction jaw motions.

5. The sleep apnea treatment system of claim 1, wherein adjustment of the positioning of the rails on the lower support side changes a protrusive orientation of the lower dental arch to the upper dental arch of a patient fitted with the upper jaw piece and the lower jaw piece.

6. The sleep apnea treatment system of claim 1, wherein the array has an attachment point spacing of 0.5 to 2.0 mm.

7. The sleep apnea treatment system of claim 5, wherein the array allows for adjustment of a protrusive orientation of the lower dental arch to the upper dental arch of a patient fitted with the upper jaw piece and the lower jaw piece by 2.5 to 15 mm.

8. The sleep apnea treatment system of claim 1, wherein the upper tooth side conforms to an upper dentition and the lower tooth side conforms to a lower dentition.

9. The sleep apnea treatment system of claim 1, wherein the upper support side and/or the lower support side comprises a metal sub-layer.

10. The sleep apnea treatment system of claim 1, wherein the upper tooth side and/or the lower tooth side comprises a biocompatible polymer.

11. The sleep apnea treatment system of claim 10, wherein the biocompatible polymer is at least one selected from the group consisting of a nylon, a polyolefin, a polyolefin-vinyl acetate copolymer, and a polyacrylate.

* * * * *